United States Patent [19]

Niemann et al.

[11] 4,135,816

[45] Jan. 23, 1979

[54] METHOD AND APPARATUS FOR DETERMINING THE TOTAL PROTEIN CONTENT OR INDIVIDUAL AMINO ACIDS

[75] Inventors: Ernst-Georg Niemann, Garbsen; Dirk Christoffers; Bernd Georgi, both of Hanover, all of Fed. Rep. of Germany

[73] Assignee: Gesellschaft für Strahlen- und Umweltforschung mbH, Neuherberg, Fed. Rep. of Germany

[21] Appl. No.: 763,688

[22] Filed: Jan. 28, 1977

[30] Foreign Application Priority Data

Jan. 28, 1976 [DE] Fed. Rep. of Germany ....... 2603069

[51] Int. Cl.$^2$ .................. G01J 3/30; G01N 21/38
[52] U.S. Cl. ........................... 356/317; 250/461 B
[58] Field of Search .............. 356/85, 98; 250/458, 250/459, 461 R, 461 B

[56] References Cited

U.S. PATENT DOCUMENTS

| | | | |
|---|---|---|---|
| 3,971,951 | 7/1976 | Rikukawa et al. | 350/458 |
| 3,973,129 | 8/1976 | Blumberg et al. | 250/461 B |
| 4,036,946 | 7/1977 | Kleinerman | 250/458 |
| 4,055,768 | 10/1977 | Bromberg | 356/85 |

OTHER PUBLICATIONS

"Meas. of Fluorescent ... Spectrophotometer"; Huke et al.; Josa; vol. 43; May 1953, pp. 400–404.

*Primary Examiner*—Vincent P. McGraw
*Attorney, Agent, or Firm*—Spencer & Kaye

[57] ABSTRACT

Method for determining the total protein content or individual amino acids in flour, cereal flour and/or leguminous products or other substances by means of fluorescence analysis. The proteins and/or the individual amino acids are treated to attain a fluorescent effect or are self-fluorescent. The proteins and/or the individual amino acids are brought into suspension in their unpretreated form. The suspension is then fluorometrically measured by means of vertical transillumination. An apparatus is provided for practicing the method and comprises a primary radiation source for emitting a primary radiation to excite the fluorescent material, optical means for directing the primary radiation in a vertical direction onto the proteins and/or amino acids in suspension, at least one vessel for holding the suspension, through which the primary radiation can pass in a vertical direction, and receiving means and evaluating means for measuring the fluorescent radiation.

17 Claims, 6 Drawing Figures

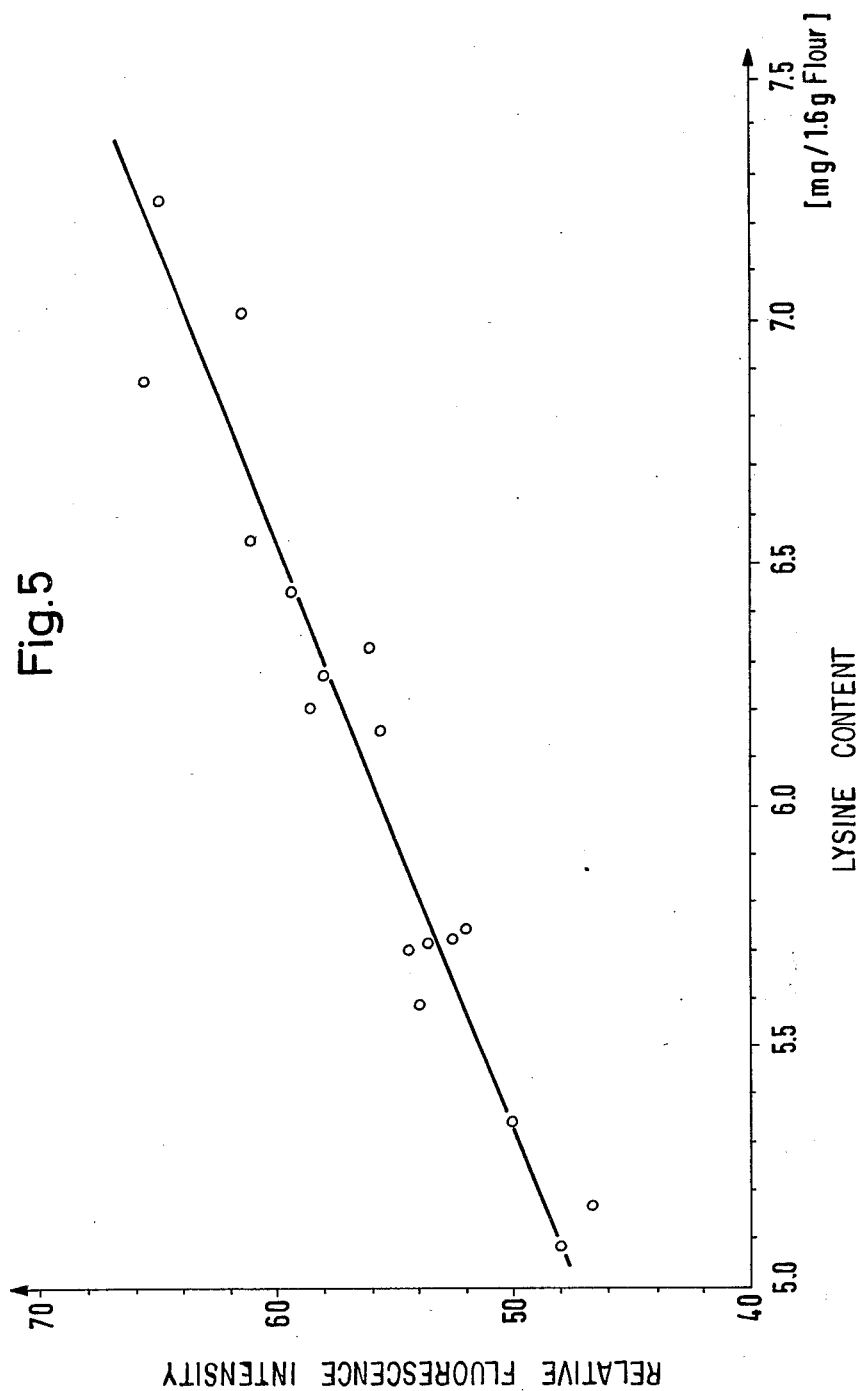

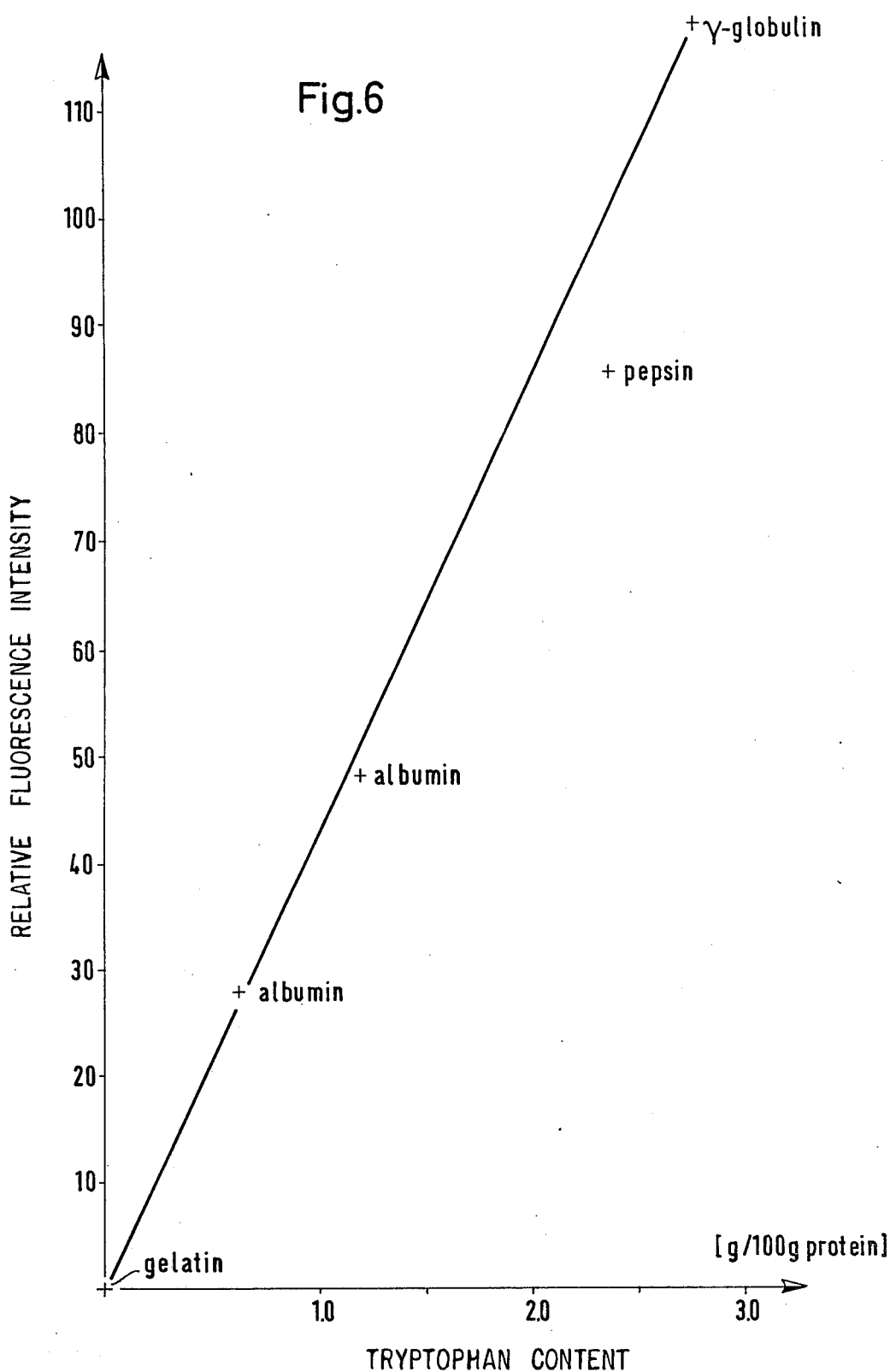

METHOD AND APPARATUS FOR DETERMINING THE TOTAL PROTEIN CONTENT OR INDIVIDUAL AMINO ACIDS

BACKGROUND OF THE INVENTION

The present invention relates to a process for determining the total protein content or individual amino acids in flour, cereal flour and/or leguminous products by means of fluorescence analysis, the proteins and/or the individual amino acids being treated to attain a fluorescent effect or are themselves fluorescent, as well as to an apparatus for practicing the method.

In the breeding of plants with the aim of increasing the quantity and quality of proteins, it is necessary to develop fast and accurate analysis methods to determine the total protein content or individual amino acids therein. This necessity is a result of the poor food situation in the world. The previously employed methods, which are substantially of the chemical type or are activation analytic, have been found to be too slow, inaccurate and are connected with substantial amounts of work. In the prior methods, a total protein determination is generally effected by initially making a chemical or activation analytic nitrogen determination and then calculating the total protein content via numerical factors. This calculation, however, also includes nitrogen which is not bound to proteins.

In the majority of determination methods employed in plant breeding, e.g. for determining lysine, the proteins are hydrolized. An exception is the dye binding capacity method (DBC). In the methods where the proteins are hydrolized, the flour samples are generally decomposed in constantly boiling 6N hydrochloric acid. Alkali and enzymatic hydrolysis can also be used. In addition to the great expenditures of time and money, the hydrolysis step also produces errors from incomplete separation of the amino acids, and a racemization and destruction of part of the amino acids. The hydrolyzate can be examined as to its lysine content by a series of different tests.

Chromatographic and electrophoretic determination methods have been used but are expensive and require practical experience. Since they furnish the total composition of the proteins, however, they are of advantage for the breeder who also wants to be informed about other essential amino acids. The separation of the hydrolyzate can be effected by paper chromatography, column chromatography or electrophoresis. The quantitative determination of the individual amino acids is usually effected colorimetrically after dying with ninhydrine. See, for example, S. Blackburn, "Amino Acid Determination" Marcel Dekker, Inc. New York (1968).

Another prior art method which involves hydrolysis is the FDNB method which is based on the reaction of fluoro-2, 4-dinitrobenzol (FDNB) with free amino groups of proteins and peptides in alkali solution. After the hydrolysis, dinitrophenyl amino acid is obtained which includes $\epsilon$-DNP-lysine. The quantitative determination of the latter is effected colorimetrically. See, for example, K. J. Carpenter, Biochemical Journal, 77 (1960) 604.

In still another prior art determination method, bacteria have been grown for enzymatic determination which produce specific decarboxylases of lysine and other amino acids (E. F. Gale, Advances in Enzymology 6 (1946) 1). L-lysine decarboxylases are obtained from bacterium cadaveris. Manometric determination of the $CO_2$ provides the lysine content of the hydrolyzate. This method also is expensive and time consuming.

In a further prior art determination method based on biologic determination, an essential amino acid is withheld from the nutrient medium of a bacteria culture so that growth will stop. After addition of an amino acid, hydrolyzate growth is proportional to the proportion of the amino acid lacking in the nutrient medium. This method is simple and very specific but does not attain high reproduceability (A. E. Bolinder, Acta Pharm. Suec. 7, (1970) 125).

For the routine lysine determination in cereal flours, the already-mentioned dye binding capacity method (D. C. Udy, Cereal Chemistry 33 (1956) 191) has found widest acceptance. In the dye binding capacity method, the sample to be examined is ground and mixed with a dye solution of orange G (7-hydroxy-8-pheylazonaphthaline disulfonic acid-(1,3)-disodium salt) of known concentration. THe dye reacts with the basic amino acids, lysine, histidine and arginine. After draining of the dye, the concentration of the unbound dyestuff in the filtrate is determined. The difference in concentration leads to a conclusion regarding the quantity of basic amino acids. It is clear that the values obtained in this way have a high correlation to the total protein content of the flour samples. The total protein content might be determined by a nitrogen determination according to Kjeldahl where 16 g nitrogen correspond to approximately 100 g protein. The advantage of the DBC method is in the avoidance of hydrolysis. It is therefore simple, quick and furnishes easily reproduceable results. Its drawback, however, is that it is not specific, e.g. for lysine. High DBC values may also be caused by high proportions of arginine and histidine and a low lysine content.

A fluorometric determination of basic and total proteins by means of sulfoflavine is also known (U. Leemann and F. Ruch, Journal of Histochemistry, Cytochemistry, 20, 659–671, 1972). This fluorometric analysis method could be transferred, with some modifications, from histochemistry and cytology to application in connection with plant breeding, yet the known fluorometers are too complicated technically for such purposes.

For example, measurements are made with a spectral fluorometer "Fluorispec" made by the firm Baird-Atomic, Model SF 100. The initial or excitation radiation is the light from a high pressure xenon lamp. In order to spectrally divide the excitation and fluorescence radiation, two double monochromators of the Czerny-Turner type with dispersion ranges of 220 nm to 700 nm are used. Each one contains two planar reflection grids. The blaze angles are designed for 300 nm on the excitation side and for 500 nm on the emission side. The fluorescence radiation is measured at a right angle to the direction of impingement of the excitation radiation.

The curves recorded by this fluorometer, however, do not represent the true fluorescence spectra of the substance to be examined. Rather, they are falsified by the wavelength dependent sensitivity of the photomultiplier employed and by the selective effect of the emission monochromator (blaze angle). Analogously, the excitation spectra are distorted by the nonconstant spectral intensity distribution of the high pressure xenon lamp and by the selectivity of the excitation monochromator. For evaluation, the measured spectra generally must be corrected. A prerequisite for breeding success is therefore, for example, that the lysine content or the tryptophan content of the seed material be determined with sufficient speed and precision during the various selection states. The above-mentioned known fluorometer is unnecessarily complicated and expensive for these protein and/or amino acid determinations in cereal flours. Moreover, sedimentation of the flour would begin and would lead to considerable measuring errors as a result of the horizontal path of the beams in the instrument.

SUMMARY OF THE PRESENT INVENTION

It is an object of the present invention to provide a specific fluorochromation (staining with a fluorescent dye) of proteins and/or amino acids and to develop a simple, inexpensive and fast fluorescence determination method for determining the presence of proteins and/or amino acids.

A further object of the present invention is to provide a fluorometer for measuring fluorescence from proteins and/or amino acids and which is so designed so that settling flour particles will not leave the measuring volume and so that the intensity maximum of the light source lies in the range of the excitation maximum of the samples, which are, for example, danzylized, mixed with brilliant sulfoflavine or are self-fluorescent.

Another object of the present invention is to provide a fluorometer in which fluctuations in intensity as a result of fluctuations in the lamp intensity are compensated by an effective compensation device.

Additional objects and advantages of the present invention will be set forth in part in the description which follows and in part will be obvious from the description or can be learned by practice of the invention. The objects and advantages are achieved by means of the processes, instrumentalities and combinations particularly pointed out in the appended claims.

To achieve the foregoing objects and in accordance with its purpose, as embodied and broadly described, the present invention provides a method for determining the total protein content or individual amino acids in flour, cereal flour and/or leguminous products or other substances by means of fluorescence analysis, the proteins and/or the individual amino acids being treated to attain a fluorescent effect or being self-fluorescent, comprising: forming a suspension of the proteins and/or the individual amino acids in their unpretreated form, then subjecting the suspension to vertical transillumination to emit fluorescence, and then measuring the emitted fluorescence.

In a preferred embodiment of the method of the present invention, the proteins and/or the individual amino acids are colored with dansyl chloride and/or sulfoflavine to form a fluorescent material.

The present invention also provides apparatus for determining the total protein content or individual amino acids in flour, cereal flour and/or leguminous products or other substances by means of fluorescence analysis, the proteins and/or the individual amino acids being treated to attain a fluorescent effect or being self-fluorescent, and being in suspension; comprising: a primary radiation source for emitting a primary radiation to excite the fluorescent material; optical elements for directing the primary radiation onto the proteins and/or amino acids in suspension; at least one vessel for holding the suspension, and through which the primary radiation can pass in a vertical direction; and receiving means and evaluating means for measuring the fluorescent radiation.

In a preferred embodiment of the apparatus of the present invention, the primary radiation source is a high pressure mercury lamp and the optical elements comprise a deflection mirror located above the vessel to deflect the primary radiation from a first direction to a vertical direction and at least one lens between the primary radiation source and deflection mirror. Preferably, two lenses are provided between the primary radiation source and deflection mirror and a fixed filter is provided between the lenses and the primary radiation source. Moreover, in another preferred embodiment of the apparatus according to the invention, the vessel may be removably mounted in a sample holder, a cavity being provided in the sample holder to accommodate receiving means in the form of a photoelement which is connected with the evaluation means.

In one preferred embodiment of the apparatus according to the present invention, the sample holder comprises a holder housing and a sample changer in the form of a slide holding at least two vessels. The slide is movably mounted in the holder housing so that one or the other of the two vessels can be brought into vertical alignment with the vertical beam of primary radiation. Moreover, the slide can be provided with passage openings below the vessels. The holder housing preferably has a cavity in its interior which cavity has an opening at its top, and the passage openings in the slide are brought into alignment with the top opening of the cavity of the holder housing. The receiving means preferably is attached below the top opening of the cavity of the holder housing, and at least one additional filter is provided in the holder housing above the receiving means and below the vessel. It is also possible to dispose the deflection mirror at the sample holder itself, above the top opening of the cavity of the holder housing.

It is to be understood that both the foregoing general description and the following detailed description are exemplary, but are not restrictive of the invention.

BRIEF DESCRIPTION OF THE DRAWINGS

The accompanying drawings, in which like numbers indicate like parts, illustrate examples of presently preferred embodiments of the invention and, together with the description, serve to explain the principles of the invention.

FIG. 5 is a plot of the relative fluorescence intensity of 1.6 grams of various dansylized wheat flours in dependence on their lysine content.

FIG. 6 shows a calibration curve for purified proteins plotted as a function of their tryptophan content in grams per 100 g protein.

DETAILED DESCRIPTION OF THE PREFERRED EMBODIMENTS OF THE INVENTION

In the practice of the present invention, a suspension is formed of the substance whose total protein content or individual amino acids are to be determined, and the suspension is placed in a transparent vessel or cuvette which is then inserted into a fluorometer. As described in greater detail hereafter, the substance is either self-fluorescent or is treated to attain a fluorescent effect.

Figure 1:
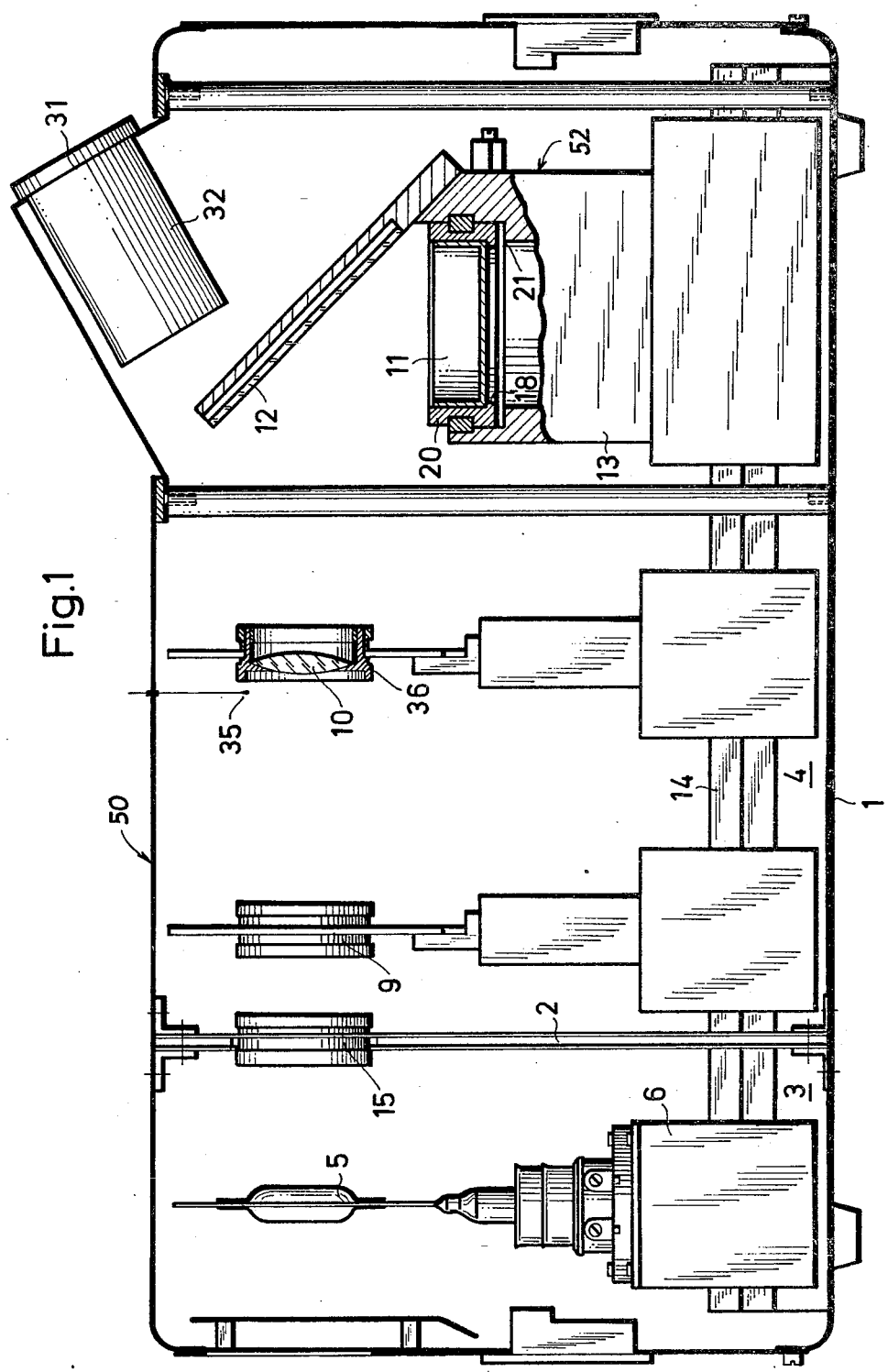
FIG. 1 is a vertical elevational view of a fluorometer produced in accordance with the teachings of the present invention for practicing the method of the present invention.
Figure 2:
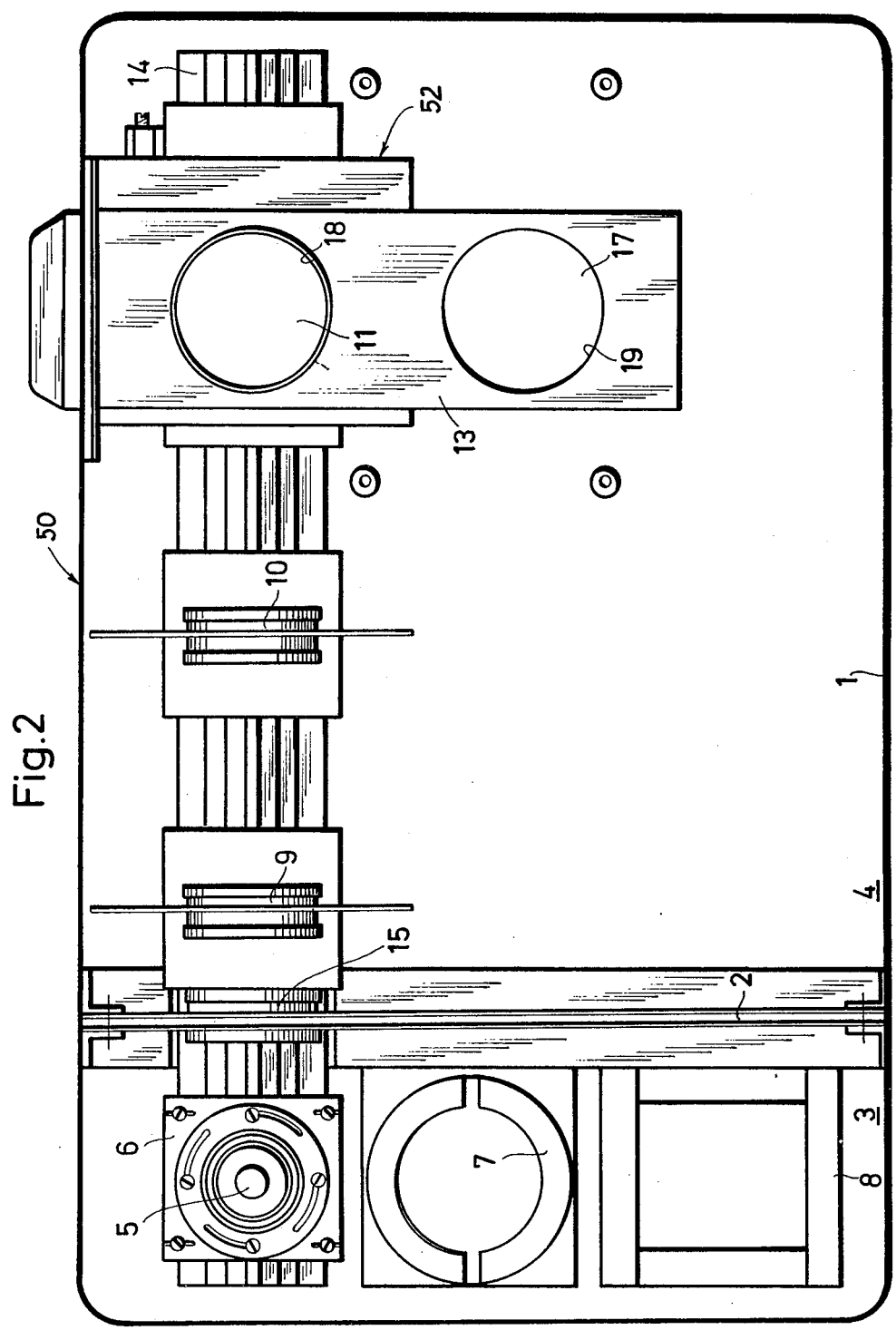
FIG. 2 is a top plan view of the fluorometer of FIG. 1.

Referring to FIGS. 1 and 2, there is shown a fluorometer, generally 50, which is accommodated in a closed housing 1, that can be divided into two sections 3 and 4 by means of a partition 2. Fluorometer 50 includes a primary radiation source for emitting a primary radiation to excite the fluorescent material. As here embodied, the primary radiation source is a high pressure mercury lamp 5 which has a base 6 and which is housed in section 3 of housing 1. Mercury lamp 5 is a quartz lamp and forms an arc which emits a horizontal beam of radiation. Section 3 further contains a ventilator 7 and an inductor 8 as shown in FIG. 2. Section 4 of housing 1 substantially accommodates optical means for directing the primary radiation in a vertical direction and a sample holder, generally 52, for holding a vessel 11 which contains the fluorescent material as described in greater detail hereafter.

In the embodiment of the invention shown in the drawings, the optical means for directing the primary radiation in a vertical direction onto the proteins and/or amino acids in suspension include a deflection mirror 12 which is located above vessel 11 which holds the suspension. At least one lens element is provided between mercury lamp 5 and deflection mirror 12. As shown in FIG. 1, a first lens 9 is provided between mercury lamp 5 and deflection mirror 12 and a second lens 10 is provided between first lens 9 and deflection mirror 12. Lenses 9 and 10, deflection mirror 12 and the arc of mercury lamp 12 are in horizontal alignment with each other and deflection mirror 12 is in vertical alignment with vessel 11. Deflection mirror 12 can be, for example, a surface mirror of a size of 100 × 65 and a thickness of 2.5 mm. Lenses 9 and 10 preferably are made of glass.

The arc of high pressure mercury lamp 5 is reproduced in the plane of lens 10 by means of lens 9. Lens 10 in turn reproduces the arc of mercury lamp 5 onto deflection mirror 12 which deflects the beam path (not shown in detail) from the horizontal to the vertical direction so that the beam path passes through vessel 11. The high pressure mercury lamp 5, lenses 9 and 10, sample holder 52, deflection mirror 12 and vessel 11 are seated on a common optical bank 14. With this optical system, the vessel contents are homogeneously illuminated. A filter 15 is further provided in partition 2 so as to be included in the beam path. Filter 15, shown in FIGS. 1 and 2, is an excitation filter, and can be comprised of a first filter element UG 1 of a thickness of 2 mm in conjunction with a second filter element BG 12 of a thickness of 2 mm, made by the firm Schott, Mainz, Federal Republic of Germany. Excitation filter 15 acts to transmit light having a wavelength which corresponds to the excitation wavelength of the fluorescent material and blocks out light which does not have such a wavelength. Thus, mercury lamp 5 does not have to be selected with a quartz optic which gives rise only to the excitation wavelength of the fluorescent material. Thus, for example, if the fluorescent material has an excitation wavelength of $\lambda = 356$ nm, mercury lamp 5 does not have to give rise only to wavelength of 365 nm, and instead filter 15 is selected to obtain such a wavelength.

A suspension of flour can be colored to attain a fluorescent effect and disposed in vessel 11 and is excited by the primary radiation from high pressure mercury lamp 5 to emit a fluorescent radiation. The relative fluorescence intensities of the colored flour samples are measured by receiving means in the form of a selenium element 16, shown in FIG. 3, which is vertically aligned with deflection mirror 12 and which is mounted in sample holder 52 below vessel 11.

Figure 3:
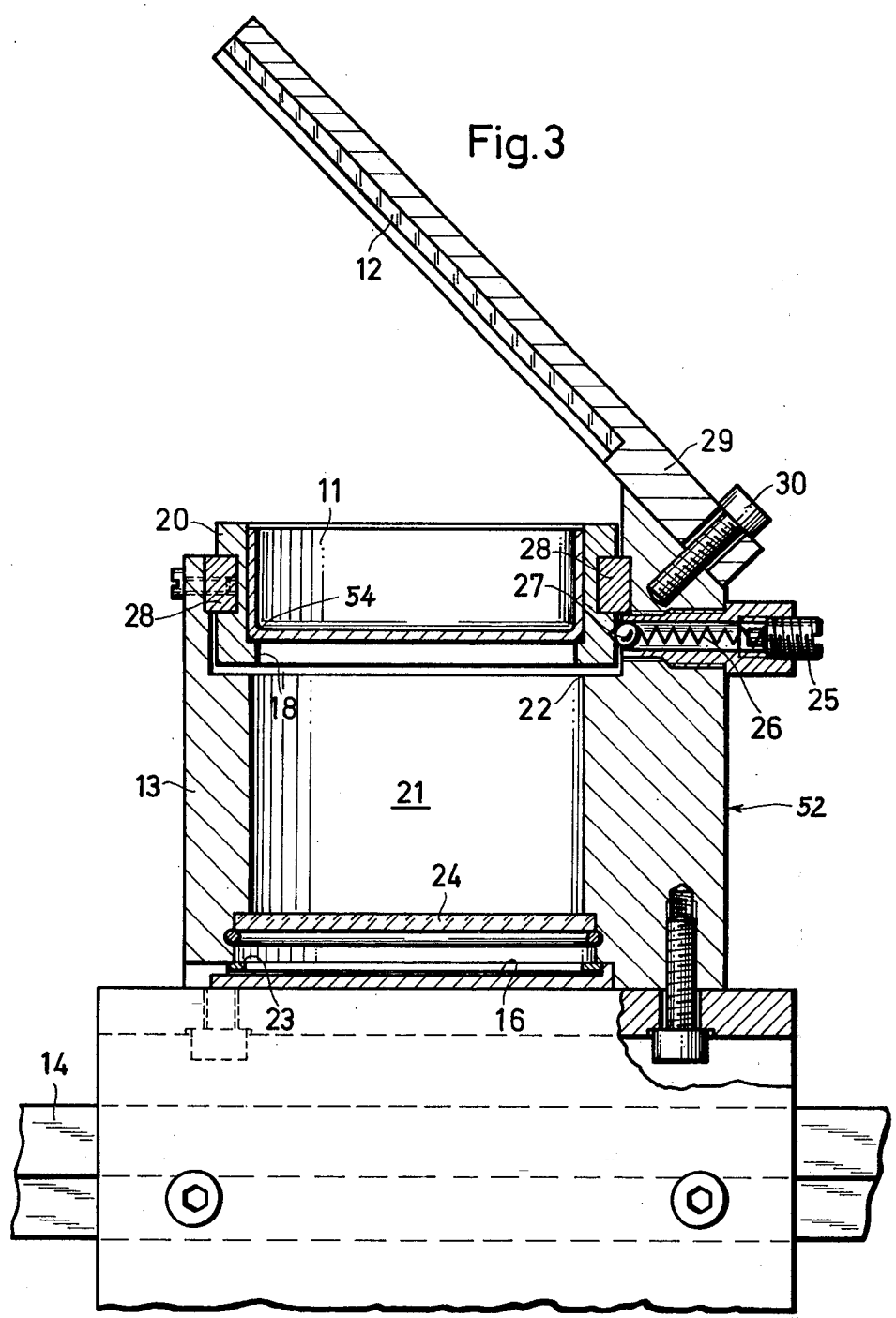
FIG. 3 is a vertical sectional view showing the sample holder of FIG. 1 in greater detail.

In a preferred embodiment of the invention, vessel 11 is removably mounted in sample holder 52, best seen in FIG. 3. Sample holder 52 comprises a holder housing 13 and a sample changer in the form of a slide 20. Slide 20 holds vessel 11 and a second vessel 17. Vessels 11 and 17 can be made of a transparent vinyl or glass material such as sold under the trade name Duran of the firm Schott, Mainz, Germany. Slide 20 is provided with an opening 18 below vessel 11 and an opening 19 below vessel 17. Vessels 11 and 17 rest on shoulders 54, formed at the top of openings 18 and 19, as best seen in FIG. 3 with reference to vessel 11. The top of holder housing 13 contains two horizontal guide rails 28 on opposite sides and rails 28 serve as guides for slide 20 to enable slide 20 to be placed horizontally within the fluorometer. Slide 20 can be displaced with respect to holder housing 13 from outside housing 1 so that either vessel 11, or vessel 17 which can contain a calibration sample, can be brought into a measuring position in vertical alignment with deflection mirror 12 and selenium element 16. Slide 20 can be arrested in any position in holder housing 13 by means of a fixing screw 25, a spring 26 and a ball 27.

Holder housing 13 has a cavity 21 in its interior, as shown in FIG. 3. Cavity 21 has an opening 22 at its top and openings 18 or 19 in slide 20 can be brought into alignment with top opening 22. A mount 29 is fastened by means of screws 30 to the top of holder housing 13 and extends above vessel 11, opening 18 and opening 22. Mount 29 holds and positions deflection mirror 12 at a location which enables the horizontal beam of primary radiation from mercury lamp 5 to be deflected vertically downward toward cavity 21 to homogeneously illuminate the fluorescent material that is contained in the vessel 11. Selenium element 16 is mounted at the bottom of cavity 21 in holder housing 13. Selenium element 16 is fastened to holder housing 13 by means of a rubber gasket 23. An emission filter 24 is mounted in cavity 21 above selenium element 16, and below vessel 11. Emission filter 24 preferably is a nonfluorescent plastic edge filter KV 418 of a thickness of 3 mm made by the firm Schott, Mainz, Federal Republic of Germany. Emission filter 24 is selected so that it permits substantially only wavelengths of fluorescent radiation to pass through it and blocks the excitation wavelengths of the primary radiation from mercury lamp 5. Selenium element 16 is not disposed directly below vessel 11, but at a distance of about 3 cm below vessel 11. Settling flour particles therefore produce almost uniform irradiation intensities on the photoreceiver selenium element 16. The above-described design of the beam path realizes reproduceability of the measured values within ± 1%, even if the flour is unevenly distributed in the vessel.

Between deflection mirror 12 or its mount 29, respectively, and housing 1 there is disposed a measuring console 31 with a digital voltmeter 32, as shown in FIG. 1. The fluorescence intensities can here be read off directly.

Due to the great difference in wavelengths between excitation and fluorescence radiation, both radiations can be easily separated from one another in spite of the transillumination process which is often critical in this respect. The selection of filters 15 or 24, respectively, is not difficult. The fluorescence intensities of the samples in vessel 11 or of the calibration glass standard in vessel 17, respectively, are high enough that a semiconductor element, as for example selenium element 16, is sufficient as receiver. The illumination intensity at a distance of 3 cm below vessels 11 or 17 is 2 to 5 Lux depending on the sample in the vessel. A selenium element 16 can be selected which still has almost maximum sensitivity in the range of 530 nm.

Figure 4:
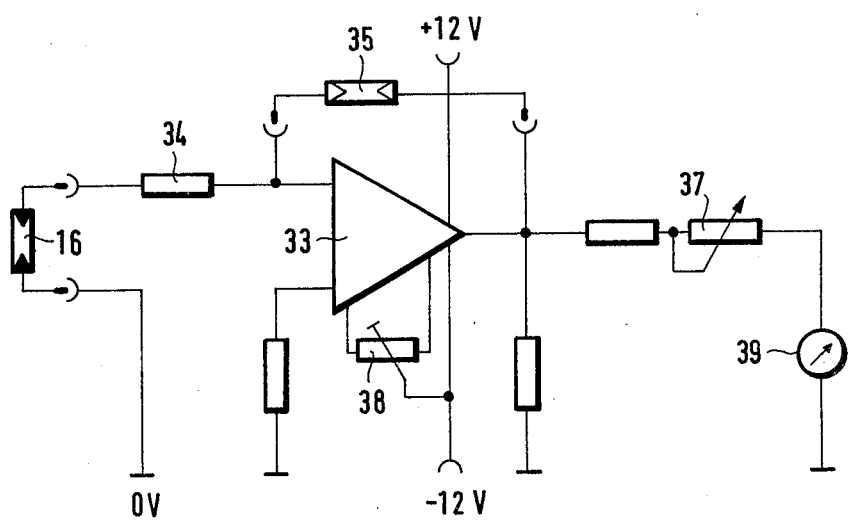
FIG. 4 is a schematic representation of a measuring and evaluating circuit for the fluorometer of FIG. 1.

The fluorometer according to FIGS. 1, 2 and 3 is completed by a measuring amplifier, shown in FIG. 4 and an inductor 8 shown in FIG. 2, for mercury lamp 5. It is not necessary to stabilize the lamp current of mercury lamp 5. Added to the intensity fluctuations as a result of changes in the mains voltage, are fluctuations caused by changes in the ambient temperature of mercury lamp 5. A falsification of the measured results by the two effects is prevented by regulating the amplification factor of the measuring amplifier inversely to the lamp intensity. For this purpose, an operational amplifier 33 (SN 72741 ITT) can be employed. It is coupled, via a 1K$\Omega$ resistor 34 to the selenium element 16 which has its other pole connected to zero. A variable feedback to amplifier 33 is provided by a photoresistor 35 (LDR 07) whose resistance is dependent on the amount of light emitted from mercury lamp 5. If the lamp intensity of mercury lamp 5 increases (the lamp is not shown in FIG. 4), for example, the resistance of resistor 35 decreases and thus the amplification decreases. Intensity fluctuations in mercury lamp 5 thus result in a change of the measuring signal reduced by a factor of 10, for example. The arrangement thus combines simple handling of a deflection method with the accuracy of a compensation method.

Photoresistor 35 is attached, for example, directly above lens 10, as shown in FIG. 1, in such a manner that the edge of the quartz bulb of the high pressure mercury lamp 5, but not the arc itself, is imaged thereon. No significant loss of intensity in the excitation radiation is connected with such an arrangement, and the stray light from the quartz bulb is sufficient for the control process. A socket 36, shown in FIG. 1, for lens 10 is designed as an aperture diaphragm. Photoresistor 35 is thus not imaged in the vessel 11 or 17, respectively, which must be illuminated homogeneously. Since the relative intensity of the spectral lines may fluctuate greatly with the pressure in lamp 5, the excitation filter 15 is placed in front of photoresistor 35. Thus, photoresistor 35 is illuminated, for example, only with the light of the 365 nm line — as is the sample in vessel 11. By inserting photoresistor 35 more or less into the arc axis of lamp 5, the amplification factor and thus the sensitivity of the circuit arrangement of FIG. 4 can be adjusted roughly. A fine adjustment, i.e. calibration of the device with the aid of a fluorescence standard, is effected by adjustment of a first potentiometer 37. A second potentiometer 38 is used to provide the zero matching with the photoelement or selenium element 16, respectively, unilluminated. A microammeter 39 (identical with the voltmeter 32 which is used as a microammeter) permits reading accuracies of better than ±0.5% of the end value on the scale. An expander circuit is therefore not required.

The low input resistance of amplifier 33, of the order of 2K$\Omega$, is significantly below the internal resistance of the selenium element 16, which is greater than 20K$\Omega$ so that the latter is practically short circuited. This provides strict linear dependence between measuring result indication and fluorescence intensity. The amplifier 33 is an operational amplifier SN 72741 of the firm JTT, USA.

The good reproduceability of the measurements with the filter fluorometer permits the determination of even slight differences, for example, in the lysine content, as they must be expected within one type of grain.

In the practice of the present invention, the substance whose protein content and/or individual amino acids are to be determined are treated to be fluorescent or are self fluorescent.

One method for treating substances to attain a fluorescent effect is to color them with a dye, and a suitable dye for this purpose is dansyl chloride. The substances to be treated initially can be in the form of seeds, and the seeds to be tested are set to a fixed water content by storing them under the same conditions. Before dying, the seeds are ground finely and homogeneously into a flour. Sample quantities of about 20 mg are selected for measurements by means of the filter fluorometer. The samples are weighed in centrifuging tubes in which they are also dyed. For this purpose, the flour is initially suspended in 0.5 N-NAHCO$_3$. After addition of 4 ml absolute ethanol, the NAHCO$_3$ is precipitated. After centrifuging, the residue is decanted. The dye solution is made freshly before every series of measurements with 1 mg dansyl chloride to 1 ml 95% ethanol and 3 ml of the dye solution are added to each sample. The dansyl chloride (5-dimethylamino-1-naphthalin sulfonyl chloride) is widely used as an end group reagent in the sequence analysis of peptides and proteins, in immunohistology and for clinical purposes. Dansyl chloride reacts with the amino end groups of the proteins as well as with the sulfhydryl (cysteine) group, the phenol (tyrosine) groups, the amino (lysine) groups and the imidazole (histidine) groups of the side chains. The dyestuff does not react with other side groups.

The flour and the dye are mixed thoroughly and the formation of lumps are avoided. The dyeing takes place at 30° C for one hour. Then the excess dyestuff is separated by three washes in ethanol. The fluorochromated flours are then suspended in 5 ml water and filled into the measuring vessel 11. The filter fluorometer is calibrated before each series of measurements by means of a glass standard in vessel 1f being placed in the illumination position during sample changing.

The fluorescence intensity increases linearly with increasing concentration up to a value of 25 mg flour per 5 ml water. Samples of about 20 mg flour per 5 ml water thus lie within the proportionality range. The relative fluorescence intensity is proportional to the quantity of lysine present in the flour samples, no matter what composition it has. Thus, the breeder can use the measured values furnished by the fluorometer directly for his selection. If he needs a measure for the protein content, he must make an additional determination of the nitrogen content e.g. by brilliant sulfoflavine or the Kjeldahl method. FIG. 5 is a plot of the relative fluorescence intensity of dansylized wheat flours in dependence on their lysine content (mg lysine/1.6g flour). The fluorescence intensities are average values of two measurements. The sensitivity of the fluorometer is set so that the glass standard produces a deflection of 50 scale divisions.

A further possible dye that can be used in the method of the present invention is sulfoflavine. Sulfoflavine is an acid dye which reacts in an acid medium with all free, positively charged protein bound amino acids. Proof of the reaction is a shift in the emission spectrum by 10 nm and a tenfold increase in the quantum yield. A further property of the sulfoflavine dye is that the proteins which are soluble in the aqueous buffer solution are precipitated. The substances dyed with sulfoflavine, e.g. barley containing 14.5% protein, selected cereals and leguminous substances, can thus be measured with the fluorometer according to the present invention.

A further possibility for use of the fluorometer according to the present invention is for self-fluorescing substances. Among these, tryptophan, for example, can be determined according to the present invention. In determining the presence of tryptophan, the tryptophan is first chemically converted to a fluorescent substance, as described in greater detail below, and an this form acts as a fluorescent dye. The analysis for tryptophan in the spectral fluorometer results in an excitation maximum of 410 nm and an emission of 500 nm for pure tryptophan and of 490 nm for protein-bound tryptophan. The tryptophan is, of course, contained as a flour in the vessels 11 or 17, respectively, of the fluorometer. FIG. 6 shows the calibration curve for purified proteins ($\gamma$-globulin, pepsin, albumin (in egg), albumin (in the cow) and gelatin) plotted as a function of tryptophan content in grams per 100 g protein.

Of advantage in determining tryptophan by the method of the present invention is the direct formation of a fluorescent substance which makes any further treatment unnecessary, such as washing and centrifuging. On the other hand, it is possible to dilute the resulting fluorescent substance with distilled water without losses in quantum yield and so that the measurement lies in the linear sensitivity range. In contradistinction to the coloring methods, tryptophan is here excited chemically to form fluorescence dyes. For this purposes concentrated $CH_3COOH$, a 95% $H_2SO_4$, Benedict's solution, $FeCl_3$, and $6H_2O$ are added to the tryptophan as reagents. The fluorescent substance is obtained after condensation and oxidation after the Adamkiewicz - Hopkins Cole reaction described by Brieskorn, C. H., Danzinger, K., in F. Lebensm. Untersuch.-Forsch. 137 (1968) 362.

Previously, it has been possible to determine tryptophan only after alkali or enzymatic hydrolysis, the latter being incomplete. After this decomposition step, a column chromatographic separation had to be effected with an amino acid analyzer. The particular drawback of such processes is the always incomplete hydrolysis, but this is avoided by the practice of the present invention.

In addition to the above-mentioned substances, it is also possible to prove the presence of tetrahymena protozoa by the method and apparatus of the present invention. 2,3,5-triphenyl 2,3,5-triphenyltetrazolum chloride (TPTZ) is quantitatively enzymatically reduced by tetrahymena protozoa to the red, unsoluble triphenyl formazan (TPF). Since TPF is fluorescent, (excitation 384 nm and emission 422 nm), it is possible to make direct measurements without prior separation of the residual components of the sample.

Various types of algae also exhibit specific fluorescence characteristics. The filter fluorometer according to the present invention can also be used to measure such algae in suspensions. The aqueous buffer solution consists of McIlvain-buffer (0.1M $C_6H_5Na_3O_7\cdot 2H_2O$ and 0.2M $Na_2HPO_4\cdot 12H_2O$) of pH 2.2.

It will be understood that the above description of the present invention is susceptible to various modifications, changes and adaptions, and the same are intended to be compre comprehended within the meaning and range of equivalents of the appended claims.

What is claimed is:

1. Method for determining the total protein content or individual amino acids in flour cereal flour and/or leguminous products or other substances by means of fluorescence analysis, the proteins and/or the individual amino acids being treated to attain a fluorescent effect or being self-fluorescent, comprising forming a suspension of the proteins and/or the individual amino acids, the proteins and/or the individual amino acids in the suspension being self-fluorescent or being in treated form in which they attain a fluorescent effect, then subjecting the suspension to vertical transillumination to emit fluorescence by passing a beam of primary radiation in vertical direction through the suspension to homogeneously illuminate the suspension, and then measuring the emitted fluorescence by a detector which is in vertical alignment with the suspension.

2. Method as defined in claim 1 wherein the proteins and/or the individual amino acids are colored with dansyl chloride and/or sulfoflavine to form a fluorescent material.

3. Method as defined in claim 1 wherein the primary radiation passes through the suspension in a downward direction.

4. Apparatus for determining the total protein content or individual amino acids in flour, cereal flour and/or leguminous products or other substances by means of fluorescence analysis, the proteins and/or the individual amino acids being treated to attain a fluorescent effect or being self-fluorescent, and being in a suspension; comprising:
 (a) a primary radiation source for emitting a primary radiation to excite a fluorescent material;
 (b) optical elements for directing the primary radiation in vertical direction onto the proteins and/or amino acids in suspension;
 (c) at least one vessel for holding the suspension and through which the primary radiation can pass in a beam of vertical direction; and
 (d) receiving means in vertical alignment with the vessel and evaluating means for measuring the fluorescence emitted from the fluorescent material.

5. Apparatus as defined in claim 4 wherein the primary radiation source is a high pressure mercury lamp and the optical elements comprise a deflection mirror located above the vessel to deflect the primary radiation from a first direction to a vertical direction and at least one lens between the primary radiation source and the deflection mirror.

6. Apparatus as defined in claim 5 wherein the optical elements comprise two spaced apart lenses between the deflection mirror and the primary radiation source and a filter is between the primary radiation source and the two lenses.

7. Apparatus as defined in claim 5 including a filter between said vessel and said receiving means.

8. Apparatus as defined in claim 4 wherein the vessel is removably mounted in a sample holder, a cavity being provided in the sample holder to accommodate the receiving means in the form of a photoelement or a photoresistor, respectively, which is connected with the evaluation means.

9. Apparatus as defined in claim 8 wherein the sample holder comprises a holder housing and a sample changer in the form of a slide which holds at least two vessels and which is movably mounted in the holder housing so that one or the other of the two vessels can be brought into vertical alignment with the vertical beam of primary radiation.

10. Apparatus as defined in claim 9 wherein the slide is provided with a passage opening beneath each vessel and the holder housing has a cavity which has an opening at its top, and the passage openings in the slide can be moved into alignment with the top opening of the cavity of the holder housing.

11. Apparatus as defined in claim 10 wherein the receiving means is attached below the top opening of the cavity of the holder housing.

12. Apparatus as defined in claim 11 including a filter in the holder housing above the receiving means and below the vessel.

13. Apparatus as defined in claim 10 wherein the deflection mirror is disposed at the sample holder above the top opening of the cavity of the holder housing.

14. Apparatus as defined in claim 4 wherein the optical elements direct the primary radiation in a downward direction.

15. Apparatus as defined in claim 4 wherein said evaluating means comprise compensating means connected to effect compensation in the evaluation result for fluctuation in the primary radiation emitted by said source.

16. Apparatus as defined in claim 15 wherein said receiving means provide a signal proportional to the intensity of the fluorescence emitted from the fluorescent material, said evaluating means comprise an amplifier having a signal input connected to receive the signal provided by said receiving means, and said compensating means are connected to said amplifier for varying its amplification factor inversely with the intensity of the primary radiation emitted by said source.

17. Apparatus as defined in claim 15 wherein said compensating means comprise a photoresistor exposed to primary radiation emitted by said source such that its resistance is a function of the intensity of such radiation, said photoresistor being connected to define a feedback path of said amplifier.

* * * * *